United States Patent
Grimont et al.

(12)

(10) Patent No.: US 6,551,776 B1
(45) Date of Patent: Apr. 22, 2003

(54) **OLIGONUCLEOTIDE SPECIFIC OF THE *ESCHERICHIA COLI* SPECIES AND METHOD FOR DETECTING AND DISPLAYING BACTERIA OF THIS SPECIES**

(75) Inventors: Patrick Grimont, Paris (FR); Béatrice Regnault, Viroflay (FR); Monique Collin, Bagneux (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 09/463,419

(22) PCT Filed: Aug. 4, 1998

(86) PCT No.: PCT/FR98/01737

§ 371 (c)(1),
(2), (4) Date: Feb. 4, 2000

(87) PCT Pub. No.: WO99/07722

PCT Pub. Date: Feb. 18, 1999

(30) Foreign Application Priority Data

Aug. 4, 1997 (FR) .............................................. 97 09961

(51) Int. Cl.[7] .......................... C12Q 1/68; C07H 21/04
(52) U.S. Cl. ...................... 435/6; 536/24.32; 536/24.3; 536/23.1
(58) Field of Search .......................... 435/6; 536/24.32, 536/24.3, 23.1

(56) References Cited

U.S. PATENT DOCUMENTS 5,595,874 A * 1/1997 Hogan et al. .................. 435/6
5,780,233 A * 7/1998 Guo et al. ..................... 435/6

FOREIGN PATENT DOCUMENTS

JP          5-192147          *  8/1993

OTHER PUBLICATIONS

Subramaniam. GenBank Accession No. U88545. Mar. 4, 1997.*
Brosius et al. PNAS USA vol. 75, No. 10, pp. 4801–4805, Oct. 1978.*
Spierings et al. Research Microbiology. 1993, vol. 144, p. 557–564.*

* cited by examiner

Primary Examiner—W. Gary Jones
Assistant Examiner—Juliet Einsmann
(74) Attorney, Agent, or Firm—Oblon, Spivak, McClelland, Maier & Neustadt, P.C.

(57) ABSTRACT

The invention concerns an oligonucleotide capable of being specifically hybridized with the ribosomal RNA (RNAr) or with the corresponding gene (ADNr) of the *Escherichia coli* genomic species (including all the Shigella genomic species except for serotype 13 *S. boydii/Escherichia fergusonii* genomic species. The invention also concerns a method for detecting and displaying the bacteria of said species.

5 Claims, No Drawings

OLIGONUCLEOTIDE SPECIFIC OF THE *ESCHERICHIA COLI* SPECIES AND METHOD FOR DETECTING AND DISPLAYING BACTERIA OF THIS SPECIES

The invention relates to oligonucleotides for the detection and visualization of bacteria belonging to the genomic species *Escherichia coli* in a sample. More particularly, it relates to an oligonucleotide capable of hybridizing specifically with the ribosomal RNA (rRNA) or to the corresponding gene (rDNA) of the genomic species *Escherichia coli* (including Shigellae with the exception of *S. boydii* serotype 13)/*Escherichia fergusonii*.

It likewise relates to a procedure for detection of the genomic species in question employing this oligonucleotide as well as the use of said oligonucleotide in a gene amplification procedure.

In this document, the term "*Escherichia coli*" (*E. coli*) denotes the genomic species (genomospecies) containing the strain-type *Escherichia coli* ATCC 11775 (=CIP 58-8). A genomic species is a collection of strains whose deoxyribonucleic acid (DNA) has a homology of more than 70% with the DNA of the strain-type of the species considered with a thermal instability of the hybridized DNA of lower than 5°0 C. (Grimont, 1988; Wayne et al., 1987). Following these criteria, the genomic species *E. coli* includes, apart from the strains usually identified as *E. coli*, the strains traditionally classed as Shigella (*S. dysenteriae, S. flexneri, S. boydii, S. sonnei*) with the exception of the serotype 13 of *S. boydii* (Brenner et al., 1973). In strictly applying these criteria, it is possible to argue that *Escherichia fergusonii* belongs to the genomic species *E. coli* (Farmer et al., 1985).

*E. coli* is usually a commensal bacterium of the colon of man and of warm-blooded animals. For this reason, its presence in a sample of water, of food, or from the environment, is interpreted as an indication of fecal contamination (indicative bacterium). Thus, an alimentary product must not contain more than a certain number of living cells of *E. coli* (being able to form a colony on a solid culture medium) in a defined mass of product (these numbers vary according to the product). For example, drinking water must not contain any living cell of *E. coli* in 100 ml (De Zuane, 1997). The counting of the *E. coli* is essential in order to estimate the hygienic quality of a food.

Strains of the genomic species *E. coli* can be pathogenic. Among these strains is found any which is commonly called Shigella, the agent of bacillary human dysentery. The strains commonly called *E. coli* can cause different infections in man or in animals according to the provision with pathogenic genes (urinary infections, choleriform or hemorrhagic diarrhea, dysentery syndrome, hemolytic and uremic syndrome, septicemia, neonatal meningitis, various purulent infections).

The identification of a strain of the genomic species *E. coli* (taxonomic identification) is important in order to question or demonstrate the fecal contamination of water or food. It is likewise important in the case where the bacterium is isolated in a normally sterile or almost sterile biological medium (urine, blood, cerebrospinal fluid, collection of fluid in a tissue or in a closed space of the body). In the open spaces of the body (digestive tract) or the feces, the presence of *E. coli* is commonplace and the identification of pathogenic factors of *E. coli* is of paramount importance in the taxonomic identification.

The taxonomic identification of *E. coli* is conventionally based on the isolation and the culture of the bacterium on a solid gelatinous medium and the application of some biochemical tests. The appearance of colonies on a gelatinous medium requires at least 18 hours. In the case of samples from the environment, culture for some days is often necessary in order that all the colonies which ought to develop appear. The application of biochemical tests starting from an isolated colony again requires 18 to 48 hours. By way of example, the counting of *E. coli* in water necessitates the filtration of a volume of water through a sterile membrane, the placing of the membrane on a semi-selective and/or indicator medium, incubation (48 hours) allowing colonies of a characteristic (but not absolutely specific) color to develop, which are then counted. As each isolated colony is supposed to be derived from a bacterial cell, the counting of the *E. coli* by volume units can be carried out. It is wise to check that the isolated colonies indeed correspond to the species *E. coli* and this requires at least 18 hours more.

Recently, techniques based on the detection of specific nucleotide sequences of the genomic species *E. coli* have been described. Thus, the detection by gene amplification (PCR type) of the gene encoding beta-glucuronidase allows the presence of *E. coli* in a sample to be identified. This method is especially used qualitatively and the interpretation of the gene amplification is frequently hampered by the possibility of contamination due to the dispersion on the apparatus and experimental tools of some nucleic acid fragments.

In situ hybridization is an interesting alternative in gene amplification. An oligonucleotide probe which is labeled (generally by a fluorescent substance) penetrates into the previously treated bacterial cells in order to facilitate this step. According to whether the ribosomal nucleic acids have or do not have a complementary (target) sequence to the probe, the probe will fix to its target and will not be removed by washing. The bacteria having retained the probe in this way become labeled (for example fluorescent) and visible by microscopic examination.

The ribosomal ribonucleic acids (rRNA) form the preferred target in hybridization in situ because of the number of copies per cell (10,000 to 30,000), which is higher than the number of copies of messenger RNA after induction (100 to 200) or of a given gene (one to several). These ribosomal RNAs (rRNAs) are identified according to their sedimentation constant (for the bacteria: 5S, 16S and 23S), present in the small subunit (16S rRNA) or the large subunit (23S and 5S RNA) of the ribosome.

The largest rRNAs are the 16S (approximately 1500 nucleotides) and the 23S (approximately 3000 nucleotides). A complementary nucleic probe of a part of an rRNA would be able to hybridize with this rRNA but also with the complementary strand of the gene (rDNA) which has encoded this rRNA. Various applications of this methodology have been published (Amann et al., 1990; DeLong et al., 1989; Giovannoni et al., 1988; Trebesius et al., 1994).

These rRNAs in fact appeared as the most appropriate molecules to serve as a molecular chronometer in the evolution of bacteria (Brenner et al., 1969; Doi & Iragashi, 1965; Moore and McCarthy, 1967; Pace & Campbell, 1971; Takahashi et al., 1967). The primary structure (sequence) of the rRNAs contains highly conserved regions and others which are hypervariable (Sogin et al., 1972; Woese et al., 1975). The perfection of a DNA-rRNA hybridization method (Gillespie & Spiegelman, 1965) has been followed by a very large number of publications applying this approach to the taxonomy and the phylogeny of bacteria and to the identification of badly classified bacteria (Johnson et al., 1970; Palleroni et al., 1973; De Smedt & De Ley, 1977).

Generally speaking, in a hybridization experiment bringing into play given sequences, the result depends greatly on the temperature and on the molarity of sodium ions of the reaction medium. For a reaction medium of given composition, an optimal hybridization temperature is defined. If the temperature is increased, the reassociated strands will finish by separating. The temperature necessary for this separation depends on the length of the perfectly hybridized (apparently perfect) part of the sequence and on its nucleotide composition. A temperature only allowing hybridization of the longest sequences is called restrictive (in opposition to optimal). Mispairings during hybridization make the thermal stability of the hybridized molecules fall.

The specificity of the hybridization in situ will therefore depend on the quality of the probe capable of recognizing and of hybridizing with a complementary sequence present in an rRNA.

Kohne et al. (1968) described a method for preparing probes reacting with the rRNA without, however, indicating how to detect *E. coli* specifically.

Göbel and Stanbridge (1984) use a cloned rDNA gene for detecting mycoplasmas contaminating tissue cultures.

Galpin et al. (1981) used the hybridization of genes encoding rRNA to detect infections with *Mycoplasma pulmonis* in mice.

U.S. Pat. No. 4,851,330 describes a strategy for obtaining nucleic acid fragments which can be used as a probe reacting with the rRNAs.

WO-A-84/02721 describes methods for detecting the microorganisms infecting a human or animal body, by using probes which hybridize with the rRNA. It is not indicated how to detect or identify *E. coli*.

Berent et al. (1985) show the interest in oligonucleotide probes in relation to cloned probes.

French Patent 2 596 774 proposes the use of a complementary oligonucleotide of the bacterial rRNA as a probe and describes two universal oligonucleotide probes.

Göbel et al. (1987) use a synthetic oligonucleotide reacting with the rRNA or its gene with the aim of identifying mycoplasmas.

U.S. Pat. No. 5,084,565 describes a so-called specific oligonucleotide probe of *E. coli*. For a target, this probe has the nucleotide zone 465 to 477 (numbering of the nucleotides according to Brosius et al. [1978]).

The probe would react with *Escherichia fergusonii* and *Shigella boydii* serotype 13 (in addition to *E. coli* and Shigella) and would not react with *Citrobacter koseri*. Nothing is said as to the reaction of this probe with the species of the genus Cedecea which are phylogenetically close to *E. coli*.

U.S. Pat. No. 5,593,841 mentions a probe reacting with the 995-1030 region of the 16S rRNA of *E. coli*. This probe reacts with *E. fergusonii* but does not react with any of the strains of *E. coli* tested and does not react with *Shigella dysenteriae*. Nothing is said as to the reaction of this probe with *Citrobacter koseri* (=*C. diversus*) and the species of the genus Cedecea which are phylogenetically close to *E. coli*.

Kwok et al. (1990) showed that a mispairing at the level of the 3' end of a primer used in gene amplification (PCR) affects the efficacy of the amplification.

Cha et al. (1992) have described a test called "Mismatch Amplification Mutation Assay" in which a primer shows a mispairing with the target sequence of a mutation to be detected, and two mispairings with the corresponding sequence of the wild allele. These mispairings concern the 3' end part of the primer. Under these conditions, their PCR system only detects the mutant allele. This method has been applied to the specific detection of *Salmonella enterica* serotype Enteritidis (Lampel et al., 1996) by creating a mispairing at the penultimate position of the 3' end of a primer.

The invention proposes an oligonucleotide for the detection and the specific and rapid visualization of bacteria belonging to the genomic species *Escherichia coli* in a sample. It therefore relates to an oligonucleotide capable of carrying out a specific hybridization with the genomic species of *Escherichia coli* (that is to say specific to all the strains of *Escherichis coli*, of Shigella (with the exception of *S. boydii* serotype 13) and of *Escherichia fergusonii*.

More particularly, this oligonucleotide is capable of hybridizing with the 637-660 region of the 16S RNA of *E. coli* (numbering system of Brosius et al., 1978). In effect, this portion of the 16S RNA is fairly well conserved in the Enterobacteria but not sufficiently to be specific to these. However, surprisingly, it turned out to be very interesting in that it allows the detection of the genomic species defined above without cross reaction with other species. The oligonucleotide according to the invention can likewise only hybridize specifically with at least 10 consecutive nucleotides of the 637-660 region of the 16S RNA of *E. coli*. In effect, with two oligonucleotides recognizing adjacent zones and then linked by a ligase, a longer oligonucleotide and therefore one which is more resistant to more stringent hybridization conditions is obtained.

It is thus possible to utilize two oligonucleotides representing the left half and the right half of one of the oligonucleotides of the invention, to make them hybridize with the target, to link them by the action of a ligase, and to increase the washing temperature so as to eliminate any small unlinked oligonucleotide. This method which reduces the background noise has been proposed by Alves and Carr (1988).

Advantageously, the oligonucleotide according to the invention corresponds to SEQ ID NO. 1.

In effect, an oligonucleotide of 24 nucleotides, complementary to the abovementioned 637-660 region of the 16S RNA of *E. coli* has been synthesized. It has been called Ec637 and identified SEQ ID NO. 1.

The labeling was obtained by a grafting of two chromophores (fluorescein or Texas Red) to each end of the oligonucleotide. The oligonucleotide probe used in in-situ hybridization at 42° C. in the presence of 22% of formamide followed by washing at 60° C. renders the cells of *Escherichis coli, Shigella dysenteriae, Shigella flexneri, Shigella boydii* (except the 13 serotype), *Shigella sonnei* and *Escherichia fergusonii* (*E. coli* genomic group) fluorescent. It does not react with the majority of the other species and genera tested. However, it has been observed that the species *Citrobacter koseri* and the species of Cedecea remain fluorescent after washing at 60° C.

In fact, a temperature of the order of 61° C. must be achieved in order that these species no longer react. However, at 61° C., the *E. coli* genomic group is rendered very weakly fluorescent.

The present invention therefore likewise relates to an oligonucleotide allowing the obtainment of results which are even better in terms of specificity.

In effect, the Ec637 oligonucleotide was modified at the level of a nucleotide situated at a conserved (invariant) position of the corresponding 16S rRNA sequence in order to create a voluntary mispairing. This mispairing was carried out in the central part of the oligonucleotide. The sequence obtained was called Colinsitu and identified SEQ ID NO. 2. The introduction of a central mispairing has the aim of weakening the hybrid which is obtained. If a sequence differs by a sole nucleotide of the 637 to 660 sequence of *E. coli*, this will cause two mispairings with the Colinsitu probe which will not hybridize under the chosen experimental conditions. This probe remains reactive with respect to the *E. coli* genomic species and becomes inactive with respect to all the other species and genera. This specificity is maintained in a wide washing temperature range extending from 51° C. to 59° C.

The Colinsitu probe can be used in in-situ hybridization but likewise, in hybridization on a filter, in liquid medium, in reverse hybridization, or as a specific primer in a gene amplification system.

The invention likewise relates to complementary oligonucleotides of the oligonucleotides described below.

Other types of labeling of the probe (radioactivity, chemical or enzymatic labeling) can be used for hybridization in situ.

More particularly, the oligonucleotides according to the invention can be labeled at their 3' or 5' end or at the 3' and 5' ends.

The advantage of this probe, applied in in-situ hybridization with microscopic examination of the bacterial cells or detection by flow cytometry, is that it is able to detect, identify and count the cells of the genomic species *E. coli* in various samples such as clinical and veterinary samples (in particular urine), water and other drinks, food, the environment.

The invention likewise relates to a procedure for detection and visualization of bacteria of the genomic species *Escherichis coli* (including all the Shigellae with the exception of *S. boydii* serotype 13)/*Escherichia fergusonii* in a sample comprising a hybridization step of the ribosomal RNA of the bacteria of said genomic species with an oligonucleotide according to the invention, and more particularly with an oligonucleotide selected from SEQ ID NO. 1 and SEQ ID NO. 2.

More particularly, the hybridization in question can be an in-situ hybridization, a hybridization on a filter, a hybridization in liquid medium or a reverse hybridization.

Reverse hybridization for the purposes of the present invention is understood as meaning a hybridization reaction in which the oligonucleotide probe of interest is immobilized on a support, the nucleic acid to be detected and/or the organism containing the nucleic acid to be detected being present in solution.

According to a particular method of carrying out a reverse hybridization reaction according to the invention, the oligonucleotide probes can be employed within a detection device comprising a matrix bank of oligonucleotides. An example of production of such a matrix bank can consist of a matrix of oligonucleotide probes fixed to a support, the sequence of each probe of a given length being situated with a gap of one or more bases in relation to the preceding probe, each of the probes of the matrix arrangement thus being complementary to a distinct sequence of the target DNA or RNA to be detected and each probe of known sequence being fixed in a predetermined position on the support. The target sequence to be detected can advantageously be radiolabeled or nonradiolabeled. When the labeled target sequence is placed in contact with the matrix device, this forms hybrids with the probes of complementary sequence. Treatment with the nuclease, followed by washing, allows the target hybrid probes-sequences which are not perfectly complementary to be eliminated.

On account of the precise knowledge of the sequence of a probe at a determined position of the matrix, it is then possible to deduce the nucleotide sequence of the target DNA or RNA sequence and consequently to detect possible localized mutations in the ribosomal DNA of *E. coli*, and more particularly mutations affecting the 637-660 region of the DNA coding for the 16S rRNA of *E. coli*.

One alternative to the use of a labeled target sequence can consist in the use of a support allowing a "bioelectronic" detection of the hybridization of the target sequence on the probes of the matrix support, when said support is formed of or comprises a material capable of acting, for example, as an electron donor at the positions in the matrix at which a hybrid has been formed. Such an electron-donor material is, for example, gold. The detection of the nucleotide sequence of the target DNA or RNA is then determined by an electronic device.

An example of production of a biosensor, such as defined above, is described in European Patent Application No. EP-0 721 016 (Affymax Technologies N.V.) or alternatively in American U.S. Pat. No. 5,202,231 (Crkvenjakov and Drmanac).

The invention likewise relates to the use of an oligonucleotide corresponding to SEQ ID NO. 1 or SEQ ID NO. 2 or differing from SEQ ID NO. 1 by a nucleotide or a complementary oligonucleotide as a primer for carrying out a gene amplification procedure, such as PCR.

The oligonucleotides according to the invention can likewise be used in a hybridization inhibition method. In effect, it is possible to envisage fixing to a support (filter, cupule or microchip) an oligonucleotide which is identical or homologous to the 637-660 region of the 16S RNA of *E. coli* and to label in any manner an oligonucleotide which is complementary to this region according to the present invention. In the absence of competitor DNAs or RNAs, the two oligonucleotides have to reassociate completely. The introduction into the system of a nucleic acid capable of reassociating with one or other of the nucleotides (for example a nucleic acid belonging to one of the species aimed at by the present invention) or both (case of two separate strands) inhibits the fixing of the oligonucleotide, which is free, labeled and according to the invention, to the support.

The present invention likewise relates to a procedure for detection and visualization of microorganisms by hybridization allowing the specificity of the oligonucleotide probe used to be optimized. In effect, an oligonucleotide is all the more specific the more net differences it has in its hybridization capacities with, on the one hand, the target sequences and, on the other hand, the other sequences. Under the experimental hybridization conditions, this difference is all the more detectable the more sequence differences (or mispairing) there are between the abovementioned oligonucleotide and the sequence with which it is capable of hybridizing. Consequently, it becomes advantageous to artificially increase the number of these mispairings by modifying the oligonucleotide used for the hybridization at the level of a nucleotide which is generally highly conserved at the level of the sequence which it is sought to detect.

Consequently, the present invention relates to a procedure for detection and visualization of microorganisms (or of a group of microorganisms) by hybridization employing an oligonucleotide which is complementary to the target sequence of the microorganism with the exception of a nucleotide located in the central part of said oligonucleotide. The nucleotide in question is located in an invariant position of the target sequence of the microorganisms and is preferably in a central position.

For example, for a complementary oligonucleotide with a length of 20 base pairs, the noncomplementary nucleotide is located between positions 7 and 13 inclusive according to a numbering of the oligonucleotide commencing at its N-terminal end, preferably, the nucleotide in question is located at position 10.

The invention therefore relates to a procedure for detection and visualization such as described above applied to bacteria of the genomic species *Escherichia coli* (including all the Shigellae with the exception of *S. boydii* serotype 13)/*Escherichia fergusonii*.

Thus, in the context of the present invention, the complementary oligonucleotide employed in the abovementioned procedure is an oligonucleotide according to the present invention and differing from SEQ ID NO. 1 only by one oligonucleotide and preferably corresponding to SEQ ID NO. 2.

Among the potential applications of the invention, the following will be mentioned more particularly:

Search for confirmation that the atypical strains of *E. coli* definitely belong to this species. The Reference Centers often receive strains which could be atypical *E. coli*. They give unusual biochemical reactions for this species such as negative reaction for the production of indole or of gas, the hydrolysis of o-nitrophenol-β-galactopyranoside, the hydrolysis of beta-glucuronides, unusual fermentation reactions, or very poor growth in the usual media. The Colinsitu probe can confirm whether these strains belong to the genomic species *E. coli-E. fergusonii*. If the reaction with the probe is positive, it is easy to distinguish *E. fergusonii* by the fermentation of adonitol and of cellobiose;

detection, identification and counting of *E. coli* in the urine of sick people or infected animals. The majority of urinary infections being due to *E. coli* and a urinary colonization or infection being characterized by the presence of more than 1000 or 10,000 bacteria per ml, hybridization in situ with Colinsitu of an appropriate dilution of urine should allow the presence of *E. coli* to be confirmed and for it to be counted in the urine in 2 to 3 hours;

detection and counting of *E. coli* in water and food. *Escherichis coli* is the principal biological indicator of fecal contamination of water and of food. It suffices to filter a known and sufficient quantity of water and to carry out the hybridization in situ on the filters thus obtained. If, with the aid of a micrometer and a reticule, the filtered volume related to a surface observed in the microscope is known, it is possible to quantify the number of cells of *E. coli* in the water. In the case of foods which cannot be filtered and which must not have one *E. coli* per 25 g, enrichment can be necessary starting from 25 g of food; in situ hybridization then carried out on the culture medium will indicate if *E. coli* is present.

The invention is not limited to the above description but encompasses all the variants thereof. The examples below allow it to be better understood while only being mentioned in purely by way of illustration.

EXAMPLES

Bacterial strains used

In total, 208 strains were used to evaluate the specificity of the probes.

The authenticity of the strains was verified by reidentifying them on Biotype-100 galleries (BioMérieux, La Balme-les-Grottes, France). The galleries were inoculated according to the instructions of the manufacturer. Automatic identification was achieved owing to the Recognizer program (Taxolab Institut Pasteur, Paris) and a Macintosh Powerbook 5300ce computer (Apple Computers).

Example 1

In-situ Hybridization

In the course of the tests, a sequence of 23 nucleotides called Ec465, 5'-GGT AACG GTC AAT GAG CAA AGG TA-3', recognizing the 465 to 487 region of the 16S rRNA, was also synthesized. This Ec465 sequence, corresponding to SEQ ID NO. 3, was used with the aim of comparison.

A published method (Trebesius et al., 1994) was followed with some modifications. The cultures were diluted in sterile distilled water to obtain an absorbance at 600 nm of 0.010, and 100 μl were filtered through PC filters (Millipore, St Quentin-en-Yvelines, France) of 0.22 μm. The fixing was carried out with a 3% aqueous solution of paraformaldehyde. The formamide in the hybridization mixture represented 22% of the volume. The probe was added at a concentration of 25 pmol. The hybridization was carried out at 42° C. for 2 hours. After washing (step determining the specificity: 20 min at 51° C. for Colinsitu, 60° C. for Ec637, 48° C. for Ec465), the filters were placed on glass slides, covered with 5 μl of Vectashield (Vector Laboratories, Burlingame, Calif.) and by a cover glass.

The filters mounted on slide were examined by epifluorescence using an Olympus BX60 microscope equipped with a WIBA (for fluorescein) or NG filter (for Texas Red) and with a DEI-470 color camera (Optronics).

The Table shows the results obtained by hybridization in situ with the fluorescent probes Colinsitu, Ec637, and Ec465. All the tested strains of *Escherichia coli*, Shigella (except *S. boydii* serotype 13), and *Eshherichia fergusonii*, are rendered fluorescent by the hybridization reaction using the Colinsitu probe. No other genomic species reacts. When the probe is Ec637, a reaction is obtained with *Citrobacter koseri* and the species of the genus Cedecea.

The Ec465 probe, used in comparison, reacted weakly with *E. coli* and with strains of Buttiauxella and the ewperiment was not pursued further.

The result of the in-situ hybridization, that is to say the bacterial cells rendered fluorescent, can also be visualized by flow cytometry rather than by microscopy.

TABLE

Reactions obtained with the fluorescent probes on hybridization in situ.

| | | Reaction with | | |
|---|---|---|---|---|
| Species | Strain | Colinsitu | Ec637 | Ec465 |
| *Escherichia coli* genomic species: | | | | |
| *Escherichia coli* | CIP 54.8 | + | + | +f |
| | 2430 | + | + | +f |
| | CIP 54-120 | + | + | +f |
| | CIP 54-122 | + | + | +f |
| | CIP 54-124 | + | + | +f |
| | CIP 70-59 | + | + | +f |
| | CIP 70-68 | + | + | +f |
| | O44 | + | | |
| | O52 | + | | |
| | O66 | + | | |
| | O90 | + | | |
| | O103 | + | | |
| | O108 | + | | |
| | O110 | + | | |
| | O111 | + | | |
| | O113 | + | | |
| | O119 | + | | |
| | O121 | + | | |
| | O127 | + | | |
| | O132 | + | | |
| | O135 | + | | |
| | O136 | + | | |
| | O140 | + | | |

TABLE-continued

Reactions obtained with the fluorescent probes on hybridization in situ.

| Species | Strain | Colin-situ | Ec637 | Ec465 |
|---|---|---|---|---|
| | O151 | + | | |
| | O157:H7 | + | | |
| | 96-4597 | + | | |
| | 6085 | + | | |
| | 67 Tunis | + | | |
| | K-12 HB101 | + | | |
| | H19 | + | | |
| | PMK1 | + | | |
| | H30 | + | | |
| | E32511 | + | | |
| | B2 F1 H21 | + | | |
| | OX3 H21 | + | | |
| | 412 | + | | |
| | HI 8 | + | | |
| | 96-302 | + | | |
| | 96-303 | + | | |
| | 96-301a | + | | |
| Shigella dysenteriae 1 | NCDC 1007-71 | + | + | |
| | Y6R | + | | |
| | 60R | + | | |
| Shigella flexneri 1a | CIP 54-58 | + | + | |
| Shigella boydii 15 | NCDC 965-58 | + | + | |
| Shigella sonnei | CIP 52-55 | + | + | |
| Escherichia fergusonii | 1016-74 | + | + | |
| | 85-11615 | + | + | |
| | 568-73 | + | + | |
| | 29586 | + | + | |
| | 32-96 | + | + | |
| | 1-85 | + | + | |
| Other genonmic species of the genus Escherichia: | | | | |
| Escherichia hermanii | 1158-78 | − | − | |
| | 1200-74 | − | − | |
| | 3514-77 | − | − | |
| | 980-72 | − | − | |
| E. vulneris | CDC 2524-69 | − | − | |
| | 394-83 | − | − | |
| | 875-72 | − | − | |
| E. blattae | 9005-74 | − | − | |
| Other genera | | | | |
| Budvicia aquatica | 2377 | − | − | |
| | 20186HG | − | − | |
| Buttiauxella agrestis | CUETM 77-167 | − | − | |
| B. brennerae | S1/6-571 | − | − | |
| B. cochleae | S3/1-49 | − | − | |
| B. ferragutiae | CUETM 78-31 | − | − | |
| B. gaviniae | S1/14-669 | − | − | +f |
| | CUETM 77-159 | − | − | |
| B. georgiana | CDC 2891-76 | − | − | |
| B. izardii | S3/2-161 | − | − | |
| B. nockiae | NSW 11 | − | − | |
| B. warmboldiae | NSW 326 | − | − | |
| Cedecea davisae | 005 | − | + | |
| C. lapagei | 004 | − | + | |
| C. neteri | 002 | − | + | |
| Cedecea sp. | 001 | − | + | |
| Citrobacter amalonaticus | 9020-77 | − | − | − |
| C. braakii | 80-58 | − | − | − |
| C. farmeri | 2991-81 | − | − | − |
| C. freundii | 621-64 | − | − | − |
| C. koseri (= C. diversus) | 3613-63 | − | + | − |
| | 8132-86 | − | + | − |
| | 8127-86 | − | + | − |
| C. rodentium | 1843-73 | − | − | − |
| C. sedlakii | 4696-86 | − | − | − |
| C. werkmanii | 876-58 | − | − | − |
| C. youngae | 460-61 | − | − | − |
| Citrobacter species 10 | 4693-86 | − | − | − |
| Citrobacter species 11 | 2970-59 | − | − | − |
| Edwardsiella hoshinae | 2-78 | − | − | |
| E. ictaluri | 92-7041 | − | − | |
| E. tarda | 10396 | − | − | |
| Enterobacter aerogenes | A1 | − | − | − |
| E. agglomerans group II | 3123-70 | − | − | |
| Group III (Pantoea dispersa) | 1429-71 | − | − | |
| Group IV | 1471-71 | − | − | |
| Group V | 3482-71 | − | − | |
| Group VI (Pantoea ananas) | 6070-69 | − | − | |
| Group VII | 6003-71 | − | − | |
| Group VIII | 5422-69 | − | − | |
| Group IX | 4388-71 | − | − | |
| Group X | 1600-71 | − | − | |
| Group XI | 5378-71 | − | − | |
| Group XII | 219-71 | − | − | |
| Group XIII (Pantoea agglomerans) | E20 | − | − | |
| E. amnigenus | 77-118 | − | − | − |
| E. asburiae | 1497-78 | − | − | − |
| E. cancerogenes | 2176 | − | − | − |
| E. cloacae | CIP 60-85 | − | − | − |
| | 77-21 | − | − | − |
| E. gergoviae | 16-74 | − | − | − |
| E. hormaechei | 491-62 | − | − | − |
| E. intermedium | 77-130 | − | − | − |
| E. nimipressuralis | E63 | − | − | − |
| E. persicinus | HK204 | − | − | − |
| E. pyrinus | 4205-93 | − | − | − |
| E. sakazakii | 4562-70 | − | − | − |
| E. taylorae | 2126-81 | − | − | − |
| Erwinia carotovora | 495 | − | − | |
| E. carotovora subsp. betavasculorum | E235 2122 | − | − | |
| E. chrysanthemi | SR32 | − | − | |
| | 1451 | − | − | |
| E. cypripedii | EC 155 | − | − | |
| E. mallotivora | 2851 | − | − | |
| E. nigrifluens | EN104 | − | − | |
| E. rhapontici | 1075 | − | − | |
| E. rubrifaciens | ER 105 | − | − | |
| E. stewartii | CNBP 3157 | − | − | |
| E. uredovora | 158 | − | − | |
| Ewingella americana | 23 | − | − | |
| Hafnia alvei group I | 5632-72 | − | − | |
| H. alvei group II | 4510-75 | − | − | |
| Klebsiella ornithinolytica | 626 | − | − | − |
| K. oxytoca | 131-82 | − | − | − |
| K. planticola | CIP 100751 | − | − | − |
| K. pneumoniae subsp. pneumoniae | 464 K2 | − | − | − |
| | 12-52 | − | − | − |
| | 532 | − | − | − |
| K. pneumoniae subsp. ozaenae | 10-79 | − | − | − |
| K. pneumoniae subsp. rhinoscleromatis | 475 | − | − | − |
| K. terrigena | 1 | − | − | − |
| Koserella trabulsii | 3518-73 | − | − | |
| Kluyvera ascorbata | 648-74 | − | − | |
| K. cryocrescens | 2065-78 | − | − | |
| Leclercia adecarboxylata | CUETM 77-3 | − | − | |
| | 8-82 | − | − | |
| Leminorella grimontii | 1944-81 | − | − | |
| Leminorella sp. | 3346-72 | − | − | |
| Moellerella wisconsensis | 2897-78 | − | − | |
| Morganella morganii | 25830 | − | − | |
| Obesumbacterium proteus | NCIMB 8771 CIP 104862 | − | | |

TABLE-continued

Reactions obtained with the fluorescent probes on hybridization in situ.

| Species | Strain | Colin-situ | Ec637 | Ec465 |
|---|---|---|---|---|
| *Pragia fontium* | 2434 | – | – | |
| *Proteus mirabilis* | PM1 | – | – | |
| | PR14 | – | – | |
| *P. myxofaciens* ... | | – | | |
| *P. penneri* | 8.88 | – | – | |
| *P. vulgaris* | PR1 | – | – | |
| *Providencia alcalifaciens* | 3370-67 | – | – | |
| *P. heimbachae* | 8025-83 | – | – | |
| *P. rettgeri* | 1163 | – | – | |
| *P. rustigiani* | 132-68 | – | – | |
| *P. stuartii* | 282 | – | – | |
| *Rahnella aquatilis* | 3307 | – | – | |
| *Salmonella enterica* subsp. *arizonae* | 44 | – | – | |
| *S. enterica* subsp. *diarizonae* | 41 | – | – | |
| *S. enterica* subsp. *enterica* serotype... | 6323-88 | – | – | |
| serotype... | 122 | – | – | |
| serotype... | 119 | – | – | |
| serotype Typhimurium | LT2 | – | – | – |
| serotype Gallinarum | 4-86 | – | – | |
| *S. enterica* subsp. *Houtenae* | 6700-88 | – | – | |
| *S. enterica* subsp. *salamae* | 1492-74 | – | – | |
| *Serratia entomophila* | A1 | – | – | |
| *S. ficaria* | 4024 | – | – | |
| *S. fonticola* | 5680 | – | – | |
| *S. grimesii* | 503 | – | – | |
| *S. liquefaciens* | ATCC 27592 | – | – | |
| | 275 | – | – | |
| *S. marcescens* | 504 | – | – | |
| *S. odorifera* | 1073 | – | – | |
| *S. plymuthica* | 510 | – | – | |
| *S. proteomaculans* | 3630 | – | – | |
| *S. rubidaea* | 864 | – | – | |
| *Trabulsiella guamensis* | 370-85 | – | – | |
| | 371-85 | – | – | |
| *Yersinia enterocolitica* | ATCC 27729 | – | – | |
| *Y. frederiksenii* | CIP 8029 | – | – | |
| *Y. intermedia* | 29908 | – | – | |
| *Y. kristensenii* | 9993 | – | – | |
| *Y. pestis* | EV40 | – | – | |
| *Y. pseudotuberculosis* | 29833 | – | – | |
| *Y. ruckeri* | ATCC 29473 | – | – | |
| *Yokenella regensburgei* | 2403 | – | – | |
| | 2405 | – | – | |
| Other genera: | | | | |
| Acinetobacter ... | A1745 | – | – | |
| *Aeromonas caviae* | 67.24 | – | – | |
| *Pseudomonas aeruginosa* | 63-52 | – | | |
| *Pseudomonas fluorescens* | DSM 50090 | – | – | |
| *P. putida* | 2066 | – | – | |
| *Vibrio alginolyticus* | LMG 4408 | – | – | |
| *V. anguillarum* | CIP 63-36 | – | – | |
| *V. cholerae* | CIP 62-13 | – | – | |
| *V. harveyi* | ATCC 1426 | – | – | |
| *V. hollisae* | CIP 101886 | – | – | |
| *Xanthomonas maltophilia* | 2377 | – | – | |

Legends
+ good fluorescence of the bacterial cells
+f weak fluorescence
– absence of fluorescence
(nothing) experiment not carried out.

Example 2
Gene Amplification

The Colinsitu oligonucleotide (unlabeled) and the following nucleotide (complementary to the 8-32 conserved region of the 16S rRNA) : 5'-ATT TGA AGA GTT TGA TCA TGG CTC AG-3' (SEQ ID NO. 4) were used as primer for the specific amplification of the gene encoding the 16S rRNA *E. coli*. The amplification kit "GeneAmp$^R$ DNA amplification reagent kit" (Perkin Elmer Cetus, Norwalk, Conn.) was used according to the instructions of the manufacturer, with the DNA polymerase "AmpliTaq$^R$" and a "DNA thermal cycler 480" thermocycler (Perkin Elmer Cetus). The reaction volume was 100 $\mu$l comprising 10 $\mu$l of buffer, 2.5 units of AmpliTaq, 200 $\mu$M of each nucleotide dATP, dGTP, dCTP, dTTP, 100 pmol of each primer and 30 to 50 ng of total DNA. The amplification conditions were the following:

initial denaturation at 94° C. for 3 minutes, 25 cycles of 60 s at 94° C. for the denaturation, 60 s at 65.5° C. for the reassociation, 120 s at 72° C. for the elongation. The amplification product was subjected to electrophoresis on 1.3% agarose (Appligéne, Illkirch, France). The expected size of the amplified fragment was approximately 600 base pairs. The use of this system effectively allows this fragment to be amplified specifically for the genomic species *Escherichis coli*-Shigella-*E. fergusonii*.

Example 3

Hybridization on a Filter

Hybridization on a nitrocellulose, nylon or cellulose filter is a practical method allowing a single probe to be applied to a large number (about a hundred) of samples of DNA. The hybridization can be carried out on colonies. In this case, the membrane is applied to colonies, impregnated with sodium carbonate (lyses bacteria, destroys RNA, and denatures DNA), and placed in the presence of the labeled probe in an appropriate buffer. After a sufficient exposure time (several hours), the membrane is washed, dried in the oven (to irreversibly fix the DNA) and the labeling is visualized. This method necessitates having colonies on a plate, but allows one colony reacting amongst thousands to be selected. Such a protocol allows 96 samples to be filtered on a treated membrane in the same fashion as the colonies.

Example 4

Hybridization in Liquid Medium

If a sample is treated so as to lyse the bacteria and to extract the DNA, this can be denatured and hybridized with a radioactive probe (125I, for example). The radioactivity associated with the hybridized DNA can be counted ($\gamma$ counting) after separation, by chromatography on hydroxyapatite, of the radioactivity associated with the nonhybridized probe.

Example 5

Reverse Hybridization

Oligonucleotide probes can be fixed on a support (filter, microplate, microchip). Several probes can then be available on a single support. The target gene is amplified and labeled, and the amplicon is placed under hybridization conditions with the sample group of probes. After washing and visualization of the labeling, the fixing of the labeling on one of the probes allows identification. This approach also allows the simultaneous detection of several organisms when the amplification is carried out on the DNA extracted from a multimicrobial sample (Rijpens et al., 1995). Although the published work uses the intergene space between the genes encoding the 16 and 23S rRNAs as a target, this approach is applicable to the gene encoding the 16S rRNA.

Example 6

Specificity of the Colinsitu Probe

It is now well established that the species of the genus Shigella (except *S. boydii* serotype 13) belong to the genomic species *Escherichis coli* (Brenner et al., 1973). It is therefore not surprising that the Colinsitu probe reacts with the Shigellae. In the genus Escherichia, *E. fergusonii* has 59 to 63% of homology with *E. coli* (by hybridization of the DNAs) with a thermal instability of the hybridized molecules of 4.5° C. (Farmer et al., 1985). Therefore the strains of *E. fergusonii* partially fill the criteria which would include them in the genomic species *Escherichis coli*. Let us recall that these criteria are a homology greater than or equal to 70% with a thermal instability of the hybridized molecules of lower than or equal to 5° C. (Wayne et al., 1987). These criteria must be interpreted with flexibility (Wayne et al., 1987). The Colinsitu probe is therefore strictly specific to the genomic species *E. coli* if *E. fergusonii* is admitted into this genomic species.

The comparison of the specificity of the Colinsitu probe with that of other probes which have been or could be proposed, will appear clearly with the following reference strains given by way of example:

Strains Which Can Be Visualized by Colinsitu Under the Conditions Described:

- *Escherichis coli* CIP 54.8 (=ATCC 11775)
- *Shigella dysenteriae* serotype 1 NCDC 1007-71
- *Shigella flexneri* serotype 1a CIP 54-58
- *Shigella boydii* serotype 15 NCDC 965-58
- *Shigella sonnei* CIP 52-55
- *Escherichia fergusonii* CIP 103357 (=ATCC 35469)

Strains Which Cannot Be Visualized by Colinsitu Under the Conditions Described:

- *Shigella boydii* serotype 13 CDC 1610-55
- *Escherichia vulneris* CDC 875-72 (=ATCC 33821)
- *Escherichia hermanii* CDC 980-72 (=ATCC 33650)
- *Citrobacter koseri* (=*C.diversus*) CDC 3613-63 (=ATCC 27156)
- *Citrobacter braakii* 80-58 (=ATCC 51113)
- *Cedecea davisae* CIP 80.34 (=ATCC 33431)
- *Cedecea lapagei* CIP 80.35 (=ATCC 33432)
- *Cedecea neteri* CIP 103241 (=ATCC 33855)
- *Klebsiella pneumoniae* subsp. *pneumoniae* K2
- *Obesumbacterium proteus* CIP 104862
- *Salmonella enterica* serotype Typhimurium (=*S. typhimurium*) LT2 (=CIP 60.62, ATCC 43971).

REFERENCES

Alves, A. M., Carr, F. J. 1988. Dot blot detection of point mutations with adjacently hybridizing synthetic oligonucleotide probes. Nucleic Acid Research 16: 8723

Amann, R. I., Krumholz, L., & Stahl, D. A. 1990. Fluorescent-oligonucleotide probing of whole cells for determinative, phylogenetic, and environmental studies in microbiology. Journal of Bacteriology 172: 762–770.

Berent, S. L., Mahmoudi, M., Torczynski, R. M.,

Bragg, P. W., & Bollon, A. P. 1985. Comparison of oligonucleotide and long DNA fragments as probes in DNA and RNA dot, Southern, Northern, colony and dot hybridizations. Biotechniques 3: 208–220.

Brenner, D. J., Fanning, G. R., Johnson, K. E., Citarella, R. V., & Falkow, S. 1969. Polynucleotide sequence relationships among members of the Enterobacteriaceae. J. Bacteriol. 98: 637–650.

Brenner, D. J., Fanning, G. R., Miklos, G. V., and Steigerwalt, A. G. 1973. Polynucleotide sequence relatedness among Shigella species. Int. J. Syst. Bacteriol. 23: 1–7.

Brosius, J., Palmer, L., Kennedy, J. P., & Noller, H. F. 1978. Complete sequence of a 16S ribosomal RNA gene from *Escherichis coli*. Proceedings of the National Academy of Science of the United States of America 75: 4801–4805.

Cha, R. S., Zarbl, H., Keohavong, P., & Thilly, W. G. 1992. Mismatch amplification mutation assay (MAMA): application the c-H-ras gene. PCR Methods Applic. 2: 14–20.

De Smedt, J. & De Ley, J. 1977. Intra- and intergeneric similarities of Agrobacterium ribosomal ribonucleic acid cistrons. International Journal of Systematic Bacteriology 27: 222–240.

DeLong, E. F., Wickham, G. S., & Pace, N. R. 1989. Phylogenetic stains: ribosomal RNA-based probes for the identification of single cells. Science 243: 1360–1363.

De Zuane, J. 1997. Handbook of drinking water quality. 2nd ed. Van Nostrand Reinhold, New York.

Doi, R. H. & Iragashi, R. T. 1965. Conservation of ribosomal and messenger ribonucleic acid cistrons in Bacillus species. Journal of Bacteriology 90: 384–390.

Farmer, J. J., III, Fanning, G. R., Davis, B. R., O'Hara, C. M., Riddle, C., Hickman Brenner, F. W., Asbury, M. A., Lowery, V. A., III, and Brenner, D. J. 1985. *Escherichia fergusonii* and *Enterobacter taylorae*, two new species of Enterobacteriaceae isolated from clinical specimens. J. Clin. Microbiol. 21: 77–81.

Fox et al., 1977. Comparative cataloging of 16S ribosomal ribonucleic acid molecular approach to prokaryotic systematics. International Journal of Systematic Bacteriology 27: 44–57.

Galpin et al., 1981. The use of ribosomal DNA (rDNA) hybridization for detection of Mycoplasma pulmonis in chronically infected mouse joints. Official Abstract vol. 47, No. 3.

Gillespie, D. & Spiegelman, S. 1965. A quantitative assay for DNA-RNA hybrids with DNA immobilized on a membrane. J. Mol. Biol. 12: 829–842.

Giovannoni, S. L., DeLong, E. F., Olsen, G. J., & Pace, N. R. 1988. Phylogenetic group specific oligodeoxynucleotide probes for identification of single microbial cells. Journal of Bacteriology 170: 720–726.

Göbel, U. B., Geiser, A. & Stanbridge, E. J. 1987. Oligonucleotide probes complementary to variable regions of ribosomal RNA discriminate between Mycoplasma species. Journal of General Microbiology 133: 1969–1974.

Göbel, U., Maas, R., Havn, G., Vinge-Martins, C., & Stanbridge, E. J. 1987. Synthetic oligonucleotide probes complementary to rRNA for group and species-specific detection of mycoplasmas. Israel Journal of Medical Science 23: 742–746.

G6bel, U.B. & Stanbridge, E. J. 1984. Cloned mycoplasma ribosomal RNA genes for the detection of mycoplasma contamination in tissue cultures. Science 226: 1211–1213.

Grimont, P. A. D. 1988. Use of DNA reassociation in bacterial classification. Canadian Journal of Microbiology 34, 541–546.

Johnson, J. L., R. S. Anderson, & Ordal, E. J. 1970. Nucleic acid homologies among oxidase-negative Moraxella species. Journal of Bacteriology 101: 568–573.

Kohne, D. E. 1968. Is olation and characterization of bacterial ribosomal RNA cistrons. Biophysical Journal 8: 1104–1118.

Kwok, S., Kellog, D. E., McKinney, N., et al. 1990. Effects of primer-template mismatches on the polymerase chain reaction: human immunodeficiency virus type 1 model studies. Nucleic Acid Research 18: 999–1005.

Lampel, K. A., Keasler, S. P., & Hanes, D. E. 1996. Specific detection of Salmonella enterica serotype Enteritidis using the polymerase chain reaction. Epidemiology and Infection 116: 137–145.

Moore, R. L. & McCarthy, B. J. 1967. Comparative study of ribosomal ribonucleic acid cistrons in enterobacteria and myxobacteria. J. Bacteriol. 94: 1066–1074.

Pace, B. & Campbell, L. L. 1971. Homology of ribosomal ribonucleic acid of diverse bacterial species with Escherichis coli and Bacillus stearothermophilus. Journal of Bacteriology 107: 543–547.

Palleroni, N. J., Kunisawa, R., Contopoulou, R., & Doudoroff, M. 1973. Nucleic acid homologies in the genus Pseudomonas. International Journal of Systematic Bacteriology 23: 333–339.

Rijpens, N. P., Jannes, G., Van Asbroeck, M., Herman, L. M. F., Rossau, R. 1995. Simultaneous detection of Listeria spp. and Listeria monocytogenes by reverse hybridization with 16S–23S rRNA spacer probes. Mol. Cell. Probes 9, 423–432.

Sogin, S. J., Sogin, M. L., & Woese, C. R. 1972. Phylogenetic measurement in prokaryotes by primary structural characterization. J. Mol. Evol. 1: 173–184.

Takahashi, M., Saito, M., & Ikeda, Y. 1967. Species specificity of the ribosomal RNA cistrons in bacteria. Biochim. Biophys. Acta 134: 124–133.

Trebesius, K., Amann, R., Ludwig, W., MŸhlegger, K., and Schleifer, K.-H. 1994. Identification of whole fixed bacterial cells with nonradioactive 23 S rRNA-targeted polynucleotide probes. Applied Environ. Microbiol. 60: 3228–3235.

Wayne, L. G., Brenner, D. J., Colwell, R. R., Grimont, P. A. D., Kandler, O., Krichevsky, M. I., Moore, L. H., Moore, W. E. C., Murray, R. G. E., Stackebrandt, E., Starr, M. P., TrŸper, H. G. 1987. Report of the ad hoc committee on reconciliation of approaches to bacterial systematics. International Journal of Systematic Bacteriology 37, 463–464.

Woese, C. R., Fox, G. E., Zablen, L., Uchida, T., Bonen, L., Pechman, K., Lewis, B. J., & Stahl, D. 1975. Conservation of primary structure in 16S ribosomal RNA. Nature 254: 83–86.

What is claimed is:

1. A procedure for detecting and visualizing bacteria of the genomic species *Escherichia coli*, wherein said genomic species comprises strains identified as *Escherichia coli, Escherichia fergusonii,* and all of the Shigella, with the exception of *S. boydii* serotype 13, comprising
hybridizing ribosomal RNA of the bacteria of said genomic species with an oligonucleotide comprising SEQ ID NO:2;
wherein hybridization between said ribosomal RNA and said oligonucleotide is indicative of the detection and visualization of said bacteria.

2. The procedure according to claim 1, wherein the hybridization is selected from the group consisting of in situ hybridization, hybridization on a filter, hybridization in liquid medium, and reverse hybridization.

3. The procedure according to claim 1, wherein the oligonucleotide is labeled at the 3' end, the 5' end, or both the 3' and 5' ends.

4. An oligonucleotide, which consists essentially of SEQ ID NO:2.

5. The oligonucleotide according to claim 4, which is labeled at the 3' end, the 5' end, or both the 3' and 5' ends.

* * * * *

SEQUENCE LISTING

```
<160> NUMBER OF SEQ ID NOS:  4

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 1
gagactcaag cttgccagta tcag                                           24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 2
gagactcaag attgccagta tcag                                           24

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 3
ggtaacgtca atgagcaaag gta                                            23

<210> SEQ ID NO 4
<211> LENGTH: 26
<212> TYPE: DNA
<213> ORGANISM: Artificial Sequence
```

-continued

```
<220> FEATURE:
<223> OTHER INFORMATION: Description of Artificial Sequence:synthetic
      DNA

<400> SEQUENCE: 4
atttgaagag tttgatcatg gctcag                                      26
```